United States Patent [19]

Brocklehurst et al.

[11] Patent Number: 5,739,003
[45] Date of Patent: Apr. 14, 1998

[54] DETECTION OF MICROBIAL GROWTH

[75] Inventors: Timothy F. Brocklehurst; Alan R. Mackie; David C. Steer; David R. Wilson, all of Norwich, Great Britain

[73] Assignee: The Minister of Agriculture Fisheries and Food in her Britannic Majesty's Government of the United Kingdom of Gt. Britain & N. Ireland, United Kingdom

[21] Appl. No.: 569,162

[22] PCT Filed: Jun. 24, 1994

[86] PCT No.: PCT/GB94/01370

§ 371 Date: Jan. 31, 1996

§ 102(e) Date: Jan. 31, 1996

[87] PCT Pub. No.: WO95/00661

PCT Pub. Date: Jan. 5, 1995

[30] Foreign Application Priority Data

Jun. 24, 1993 [GB] United Kingdom ............... 9313052

[51] Int. Cl.[6] .............. C12Q 1/02; C12Q 1/00; A01N 1/02; G01N 33/53

[52] U.S. Cl. .............. 435/29; 435/287.1; 435/283.1; 435/968; 435/34; 435/4; 435/805; 436/808; 396/511; 422/55; 422/68.1; 422/82.05; 430/945

[58] Field of Search .............. 435/29, 34, 244, 435/287, 808, 291, 968, 287.1, 283.1, 4, 805; 422/68.1, 82.05, 55; 430/945; 436/808; 396/511

[56] References Cited

U.S. PATENT DOCUMENTS

| | | | |
|---|---|---|---|
| 3,990,851 | 11/1976 | Gross et al. | 435/29 |
| 4,541,719 | 9/1985 | Wyatt | 435/29 |
| 4,972,258 | 11/1990 | Wolf et al. | 435/29 |
| 5,366,858 | 11/1994 | Koizumi et al. | 435/29 |

*Primary Examiner*—Louise Leary
*Attorney, Agent, or Firm*—Nixon & Vanderhye

[57] ABSTRACT

The present invention relates to a method for determination of numbers of microorganisms present in materials and for predicting their growth capability in the materials such as foodstuffs, growth media and in the presence of chemical agents. The invention also provides immobilizing cassettes and optical apparatus for use in this method.

36 Claims, 3 Drawing Sheets

DETECTION OF MICROBIAL GROWTH

The present invention relates to a method for determination of numbers of microorganisms present in materials and for predicting their growth capability in these, analogous materials such as foodstuffs, in growth media and in the presence of chemical agents. Further provided are immobilizing cassettes and optical apparatus for use in this method.

Many methods can be used for determination of the rate of bacterial growth. These can involve direct measurement of the number of viable bacteria by plating techniques, measurement of the intensity of scattered light, absorption of light or some indirect measurement of cell concentration such as ATP and bioluminescence, or electroimpedence measurement. Few of these techniques are amenable to continuous monitoring and hence they require repetitive sampling, which is often laborious and time consuming, and others are relatively insensitive and require the presence of large numbers of bacteria.

Traditional approaches to the problem of food safety have involved inoculation of a material under investigation with a suspension of a known bacterial species and measuring the number of viable cells during storage; this being known as challenge testing. Such a method gives data that is applicable only to the foodstuff actually tested. For predictive purposes relating to untested foods it is necessary to investigate factors that contribute to the growth or death of bacteria under predetermined analogous conditions to that foodstuff. Similarly, the pharmaceutical and laboratory chemicals industry has an ongoing need for methods which can select media and agents for their ability to selectively promote, support or inhibit microbial growth, or on the basis of their microbicidal activity. Drugs, e.g. antibiotics, must be screened for activity against particular microorganisms and the concentration required for achieving that effect must be determined.

It is known to use the ability of a material to scatter laser light for the purpose of studying biological materials such as proteins, cells, viruses and tissue fragments (see e.g. EP 0514178, WO 88/01736, U.S. Pat. No. 5,155,549 and U.S. Pat. No. 4,764,013) in a detection zone in a conduit. It is further known to use such ability for measuring antibody-antigen responses in a scattering cell (see e.g. EP 0064230, U.S. Pat. No. 4,799,796) and for characterising microparticles, including bacteria, and their use in indicating the presence of various agents (see e.g. EP 0102726). The known systems use sample or flow cells to contain the material under study but do not allow the study of microorganism growth in a large number of samples under a variety of conditions, nor do they address the problems of reproducibility results from such testing.

The present inventors have now provided a novel method capable of rapidly determining the presence and numbers of microorganisms in test media, and thus of predicting the growth rate of such microorganisms in these and in analogous materials. They have also provided culture immobilizing cassettes and optical apparatus which allow the rapid screening of such materials in a collocated format using the method whereby the amount of predictive data that can be generated in one step is increased. The method and apparatus particularly facilitate prediction of microbial growth in media of complex physicochemical microstructure.

Where a material, e.g. a foodstuff, has homogeneous pH, salt and/or nutrient concentration, prediction of growth of given microorganisms in it may be carried out using modelling techniques based upon results from analogous growth media studies. Such models however are not well suited to the study of materials having complex microstructure such as those containing dispersed particulates, air bubbles, liquid droplets or solid particles; many of these often occurring in a liquid continuous phase in foodstuffs. In such cases a variety of conditions require study in a statistically valid fashion.

The present invention provides a technique wherein, in a preferred predictive format, microbial colonies, e.g. bacteria, are allowed to form as spheres within a chosen media, e.g. a gelatin gel, unhindered by any surface or constraints of nutrient or oxygen limitation. Using fixed angle laser light scattering in order to determine continuously the increase in diameter of the microbial colonies within the gel cassettes, computations translate the data and derive the increase in the number of viable microorganisms within the colonies continuously with time, and such increase is used to determine the growth rate of the microorganisms.

A first aspect of the present invention provides a method for determining the characteristics of a material with respect to its ability to kill, or inhibit or support growth of, microorganisms, comprising determining the presence and/or amount of microorganisms in a body of the material or a material having one or more analogous properties thereto by passing a beam of laser light through it, processing laser light scattered by the material at a set angle or angles to provide a signal indicative of the amount and/or type of scattering, and relating this to the presence and/or amount of microorganisms, characterised in that the body comprises a solid or semi-solid medium of predetermined composition and dimension and the change in the presence or amount of microorganisms between two or more temporally spaced determinations at a given locus of the body of material is related to the material's characteristics.

Preferably, in order to maintain predetermined dimension for given conditions e.g. of temperature, the support medium is contained as a body within a cassette which comprises a container including two opposed substantially parallel retaining surfaces of laser transmitting material situated on either side of an interior volume. In this manner a number of support media may be inoculated with one or more samples containing, or suspected of containing, microorganisms, e.g. a bacteria, and these can be monitored over a period of time to study microorganism growth by placing the cassettes in path of the laser and determining changes in microorganism number from the difference in signal for a given cassette. Particularly this technique allows the microorganism content at a specific locus of a given cassette to be monitored by scanning the laser such as to pass light through two or more discrete locii of the body of the material. A locus will be understood here to refer to the volume of material that the laser is capable of assessing for microorganism content in one measuring step.

The body of the material is preferably provided with substantially parallel opposed external surfaces, and is preferably oriented at about 45° to the incident laser beam, such as to minimise the amount of scattering not produced by the medium and its microbial content. In order to maintain a focussed image of the beam throughout the thickness of the material and to keep the distance between the centre of scattering and the processing means as uniform as possible along the length of the beam therein, it is preferred to collect the light scattered through 90° for processing purposes using a processing means. This provides a similar solid angle for light collection at all points along the beam in the material. The body should preferably be mounted such that light is reflected away from the processing means so that only scattered light is processed.

A preferred method of processing collects the scattered light, for example using a microscope objective lens, and focuses it onto a photomultiplier or line charge coupled device (CCD) camera for detection. This is particularly preferably carried out by focusing the light collected onto a pinhole using a scanning device, e.g. a scanning mirror, and passing the light through the pinhole, optionally also through a filtering means, e.g. a narrow band pass filter for removing stray background light, into the photomultiplier or CCD from which the signal is derived. Use of a CCD with suitable optics to view all of the body allows the scanning mirror to be dispensed with as it allows processing of scattered light from all areas of s body to be processed from a single relative position. Output signals are advantageously fed into a computer processor unit whereby it can be stored and manipulated for deriving information relative to other measurements from the body, other bodies or later derived signals from either.

The method of the present invention is particularly effective when used to determine microbial numbers, and thereby growth or destruction, over all or part of the extent of the body of material. This is particularly effective when that body has been designed to be, or is inherently, varying in its composition and thus ability to support or inhibit microbial growth. The application of a laser light beam source allows study of the body in the form of pixels, for example of tens to several hundred µm diameter, when applied in collimated form, e.g. by passing the beam through pinhole mounted close to one of the parallel body surfaces. Although light reflected from different angles from a sample has been treated in pixel form by EP 0102726, use of a solid or semi-solid (e.g. gelled) medium target body divided into pixels has not been so attempted or utilised to advantageous effect in rapid testing.

The present method, by determining the scattering in a given pixel at any one time maximises the contribution of microorganisms, e.g. bacterial groups of only 10 µm, to the scattering with respect to the exterior surfaces of the body, any retaining layers, intrinsic properties and impurities of the medium itself.

A particular advantage of the present method is its ability to rapidly and automatically determine the presence, amount and location of microorganisms in a material, that being provided by the ability to treat the material in pixel zone fashion, moving the beam from one zone to another to scan the entirety of a whole or part of a material. This scanning is readily achieved by mechanically moving the body of material relative to the beam and light processor, and most conveniently by moving the body in X-Y fashion while holding the beam and processor fixed.

In a second aspect of the present invention there is provided a method for determining the presence and/or amount and/or characteristics of a microorganism in a material comprising inoculating a solid or semi-solid medium with a sample of the material, forming the inoculated medium into a body of predetermined dimension, passing a beam of laser light through the body, processing laser light scattered by a given locus of the body at a set angle or angles to provide a signal indicative of the amount and/or type of scattering and relating this to the presence and/or amount of microorganism and relating temporal change in presence and/or amount of the microorganism at that locus to its characteristics. This method uses any of the features of the first aspect of the invention as they apply to variation of medium capability to kill or support or inhibit microorganism growth or to the arrangement of associated laser and light processing apparatus In a preferred embodiment of the second aspect of the invention the characteristics of the microorganism so determined are used to identify its type. Still more preferred is a method where the body of material varies in its composition and thus ability to support or inhibit microorganism growth. This is particularly preferred to be carried out using a gradient of one or more agents across the body, or by exposing the body to such agents, e.g. in the form of a particular atmosphere contacting its outer surface, as described previously.

For the purpose of predicting the microorganism growth potential of a given material, or characterising a microorganism, the present inventors have provided an immobilizing cassette into which a test media may be placed for movement between the laser source and the processor. The cassette is such that it can be loaded with inoculated test media of one characteristic, or with a complex medium mimicking a complex foodstuff or set out in gradients of drug, pH, salt, nutrient or other agent content.

The cassette of the present invention comprises a container including two opposed substantially parallel retaining surfaces of laser transmitting material situated on either side of an interior volume, with at least one sealable opening provided suitable for filling the volume with a material under investigation without damaging the surfaces over at least a substantial area, preferably leaving them undamaged on the two sides. In order to enhance the regularity of the cassette it should be of rigid format, but such property can be conveniently achieved using non-rigid materials for the laser transmitting retaining surfaces when a rigid frame is provided having windows coinciding with the retaining surfaces over at least part of their area such that a laser beam can traverse the material inside the cassette in use.

Thus a convenient frame has windows on two opposed parallel sides spaced a distance suitable for passage of laser light through a variety of laser transmitting materials. This distance may be from fractions to tens of millimeters, but is conveniently of the order of 1 to 5 mm, preferably about 2 mm. Particularly preferred are thicknesses which allow diffusion of oxygen from the atmosphere into the body of the material. The other dimensions of the cassette and its frame will depend upon the volume of the material intended to fill it. Where the number of different parameters required for study is small the area of the cassette windows may be similarly small. Where tens of different concentrations are being studied it may be necessary to provide sufficient area to allow address of each of these. A convenient dimension of the frame is found to be 130 mm×145 mm×2 mm with opposed windows in the frame of 100 mm×100 mm, but possibilities are not limited.

The retaining surfaces may be of any laser transmitting material selected to pass the laser beam intended to be scattered. Where the rigid frame is used, these surfaces may be of thin plastics film, e.g. PVC, preferably as thin as its strength will allow without provision of defects that might affect the light scattering. Frames are typically of plastics and define a rectangular aperture therethrough which forms the volume; acetal is one suitable plastics for such use. Most conveniently, the cassette of the present invention is provided by enveloping a frame as described above with a sleeve of heat shrinkable plastics film such that only one end or side of the sleeve remains open, the other having been heat sealed. The sleeve is dimensioned to be slightly larger than the frame, e.g. 1.1 times each of its dimensions, and may be heat shrunk into place using heated air. The open end or side is sealed before use by heat sealing or using a mechanical clamp.

The cassette is filled with material for testing through the open end or side, or through a filling port. For studying varying parameters of agents such as drugs, or modelling foodstuff pH, salt and/or nutrient conditions, solid or semi-solid media, e.g. of gel form, are layered at desired thickness such that a series of different zones are created across the area of the cassette window. The cassette is sterilised before loading with the media, and the media are inoculated with a desired quantity of the organisms under investigation before sealing the cassette, preferably before gelling such that uniform distribution is ensured. It should be noted that selection of air permeable plastics films allows aerobic or other varied atmospheric respiration conditions to be studied.

Loading is conveniently carried out by use of a pumping system, e.g. peristaltic pump or a syringe, to feed medium through a tube and needle or nozzle assembly which is used to accurately layer it in a desired part of the cassette interior. Medium layers are allowed to set before a successive layer is added. Filling through a port, e.g. an aperture in the frame coextensive with the volume, requires that to be sealed, e.g. with tape.

The conditions under which the cassette is maintained and scanned may be influenced by housing it or the scanning apparatus as a whole within an environmentally controlled chamber, e.g. one in which gas content of its atmosphere, humidity and/or temperature are particularly controllable such that conditions suitable or desired for study of growth of a particular microorganism may be created. A particularly preferred embodiment houses the cassette in use in a chamber in which the gas content may be varied as required, e.g. using such as a flow-through chamber allowing application of different atmospheres to the gel cassette surface in situ within the apparatus housing.

In this respect the thickness of the cassette may be of varying dimension along any one or more of its profiles, and varying thickness cassettes may be accommodated for in the part of the scanner in which they are located during scanning. It is also intended that cassettes should optionally allow for a head space such that colonies can grow on the surface of the gel for study of the condition where surface growth occurs. Such surface growth may be at an interface between the solid or semi-solid and a liquid or gas phase.

In a further aspect of the invention maintained gradient cassette apparatus and cassettes are provided wherein at least one, and preferably both, of the opposed ends of the medium filled cassette are communicated with reservoirs of material having desired chemical composition. In this way a gradient of constant slope with respect to a given chemical or physical state can be maintained for longer periods than where the layering approach is used. The apparatus for this format will comprise one or more reservoirs adapted to provide constant composition medium to the interface with a cassette medium; preferably upper and lower reservoirs fed in turn by constant composition liquid medium from larger reservoirs. It will be realized that such reservoirs may be associated with the cassette or with the apparatus itself and that any number of reservoirs may be attached to the cassette in use such that the influence on a given locus of the material therein can be accurately altered.

In order to screen the whole of the cassette window area the relative movement of the cassette and laser beam is preferably achieved by mounting the loaded cassette on an X-Y stage capable of moving it in directions perpendicular to each other with the window area presented at a suitable angle to the incident beam, i.e. preferably at 45°, such that the whole of the window area may be accessed by the incoming beam.

In a further aspect of the present invention there is provided an apparatus for performing the methods of the invention comprising a source of laser light, a mounting for supporting a body comprising a solid or semi-solid material to be studied at a desired angle to the laser light emitted by the source, and a means for processing light scattered by the material over a predetermined angle and producing a signal therefrom characterised in that the apparatus is adapted to scan the laser through all or part of the volume of the body. Preferably the apparatus is adapted to receive a cassette of the present invention.

Preferably the means for processing the scattered light includes a magnifying lens which is focussed such that the light is directed into a photomultiplier. Using a CCD device it will merely be necessary to ensure that the scattered light from any given pixel of the body of material can be captured and analysed. The laser light source is preferably positioned such that a laser beam emitted by it is collimated to a desired dimension before traversing the material on the mounting, and the lens directs light either onto a scanning device which focuses it in turn through a pinhole, and preferably a stray background light filter, to the photomultiplier, or alternatively directly to the CCD.

It will be realised that many materials will not be capable of being addressed by laser beam in this manner due to their inherent opacity to laser light rendering them liable to overheating and damage under its influence. However, those skilled in the art will realize that by studying laser transmitting materials that are capable of passing laser light without absorbing amounts that would render the scattering results inaccurate, suitable solid and semi-solid media for modelling and screening will be readily provided. It will be realised that where media are being used that are analogous to the material it is intended to model, the laser opacity need not be identical to the modelled material; thus for example a laser opaque foodstuff may be modelled for pH and nutrient content by a laser transmitting medium.

For use with typical growth media the present inventors have found that a 30 mW Helium Neon laser is entirely acceptable for this purpose, but other laser sources will occur to those skilled in the art that may be more suited to these or other materials as required.

The method, cassettes and optical apparatus of the present invention will now be described by way of illustration only by reference to the following Figures and Examples. Further embodiments falling within the scope of the invention will occur to those skilled in the art in the light of these.

DETAILED DESCRIPTION OF INVENTION

EXAMPLE 1

Gel cassette system.

Figure 1:
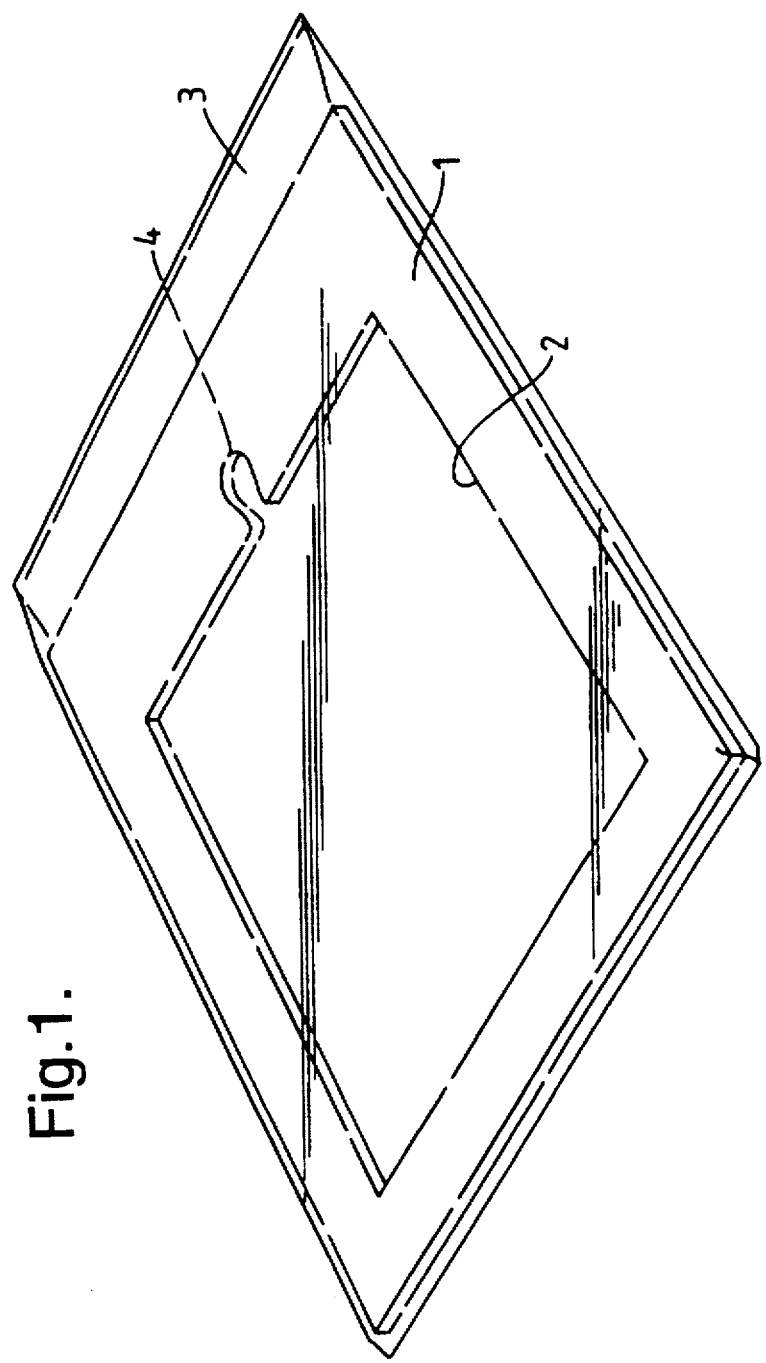
FIG. 1: shows a perspective view of a cassette of the invention as described in Example 1.

A cassette (FIG. 1) was constructed consisting of a polycarbonate (Makroion, Amari Plastics, U.K.) or acetal frame (1) which was 2 mm thick and had outer measurements of 130 mm×145 mm and a window (2) within the frame that measured 100 mm×100 mm, sealed within a sleeve (3) of polyvinyl chloride (PVC) packaging film (TSB 11, Borden, U.K.). This film was 17 μm in thickness, and was manufactured with an integral 10% stretch along its longitudinal and transverse axes. A cassette was made by enveloping the frame within a sleeve of film that was heat sealed on three sides to form an envelope that measured 1.1 times the length and 1.1 times the width of the frame. The frame was inserted into the envelope and a strip of domestic baking parchment inserted between the sheets of PVC in order to avoid adhesion of the two inner faces of the film. The envelope was sterilised by autoclaving at 121° C. for 20 mins, the cassette was removed from between the supporting stainless steel plates, the baking parchment removed aseptically, and the remaining side of the envelope around the cassette sealed. The PVC film sheet on either side of the sterile cassette was made taut in a stream of hot air. A filling port (4) was provided by way of an aperture in the frame coextensive with the space between the PVC films enclosing the window; thus allowing filling tube access. This port in turn was accessed by making an incision in the film adjacent it which was sealed with tape before scanning.

EXAMPLE 2

Filling of cassette. The cassette was filled with microbiological culture medium that was composed of Trypticase Soy broth (TSB, Baltimore Biological Laboratory) with added yeast extract and giucose (TSBYG) and gelatin (approx. 225 bloom from bovine skin, Sigma). The TSBYG was prepared at twice the final concentration and was sterilised by filtration. The gelatin was was prepared as a 20% (w/v) aqueous solution, adjusted to pH 7.0 by the addition of NaOH, 5 mol/l. and sterilised by autoclaving at 121° C. for 20 mins.

For use in a cassette the gelatin was melted by incubation at 55° C. for 20 mins, and mixed in equal volume with double strength TSBYG. In some cases the composition of the culture medium within the cassette was modified by the addition of NaCl to the TSBYG or by adjustment of the pH by the addition of sterile HCl (1 mol/l). Bacteria were added to give a suspension that contained approximately $10^3$ viable bacteria $ml^{-1}$. At this concentration the bacteria, and hence the colonies derived from them, were on average 1 mm apart so that seen in 2 dimensions in the cassette they appear on average to be 0.6 mm apart with a 2 mm thick gel.

Addition of medium to the cassette was carried out by making an incision in the PVC adjacent an inoculation port outside the window area and pumping the medium in through a tube with a needle or nozzle in its distal end under influence of a syringe and a three way tap. The cassette was cooled in order to solidify the gelatin/culture medium mixture within and then mounted in the laser gel scanner (LGS) system in a room strictly controlled at 20° C.

EXAMPLE 3

Construction and use of layered medium containing cassettes.

Figure 5:
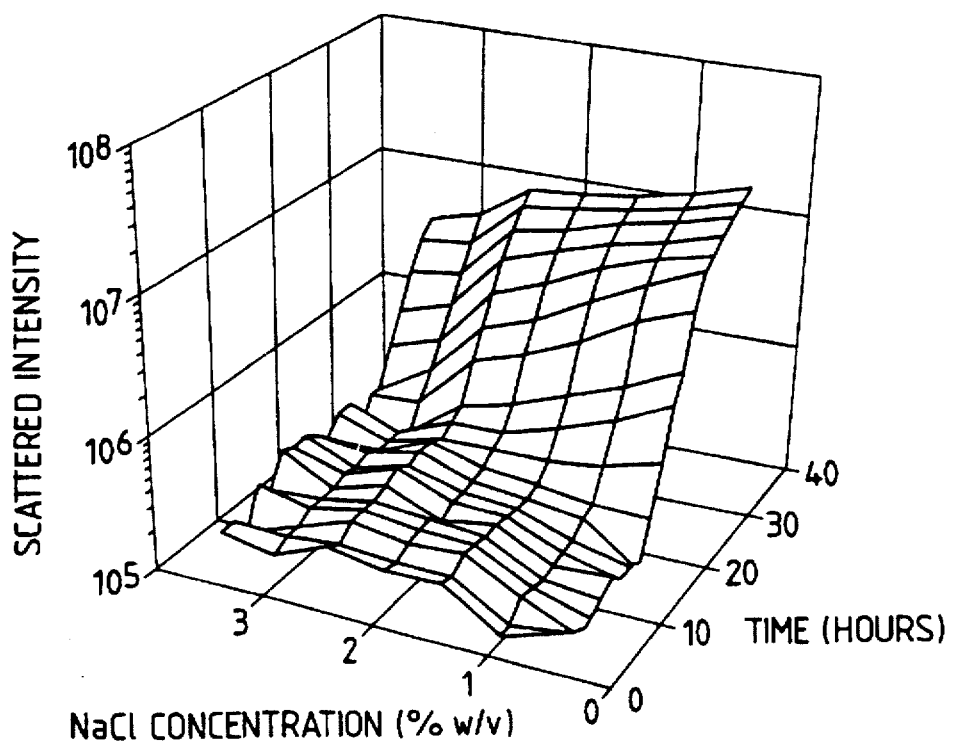
FIG. 5: shows a graph setting out the results of a growth experiment where scattering intensity produced by *Salmonella typhimurium* growth is plotted against NaCl concentration in % w/v of gel against time.

A cassette as described in Example 2 was filled layer by layer with liquid gel medium of increasing NaCl content; each layer being allowed to set before addition of the next. Analysis of NaCl content at given areas of the window was carried out after each experiment to determine the gradient lifetime for a given gradient. Using this technique pH and chemical gradients can be successfully established for several hours. The growth of Salmonella typhimurium in this cassette at 20° C. was studied using the laser scanner and the results of this study are set out in FIG. 5. Such results provided from a panel of microbes may be used as standard 'calibrations' against which growth of unknown microorganisms may be compared in the second aspect of the invention.

EXAMPLE 4

Construction of maintained gradient cassette.

A gradient former was constructed from stainless steel (see FIG. 3) having front and back plates which engage a standard gel filled cassette having incisions across the width of one PVC windows at it top and bottom. The solidified contents of the cassette were brought into contact with former reservoirs containing liquid medium having composition of study component equal to the extremes of the range being studied such that a gradient forms from top to bottom. The medium in the reservoirs was maintained at respective constant study levels by pumping medium between them and larger reservoirs containing the desired composition; the reservoir medium being sterile as opposed to the inoculated cassette medium. Leakage was prevented using rubber gaskets/seals which interface the periphery of the incisions in a liquid tight manner.

Figure 3:
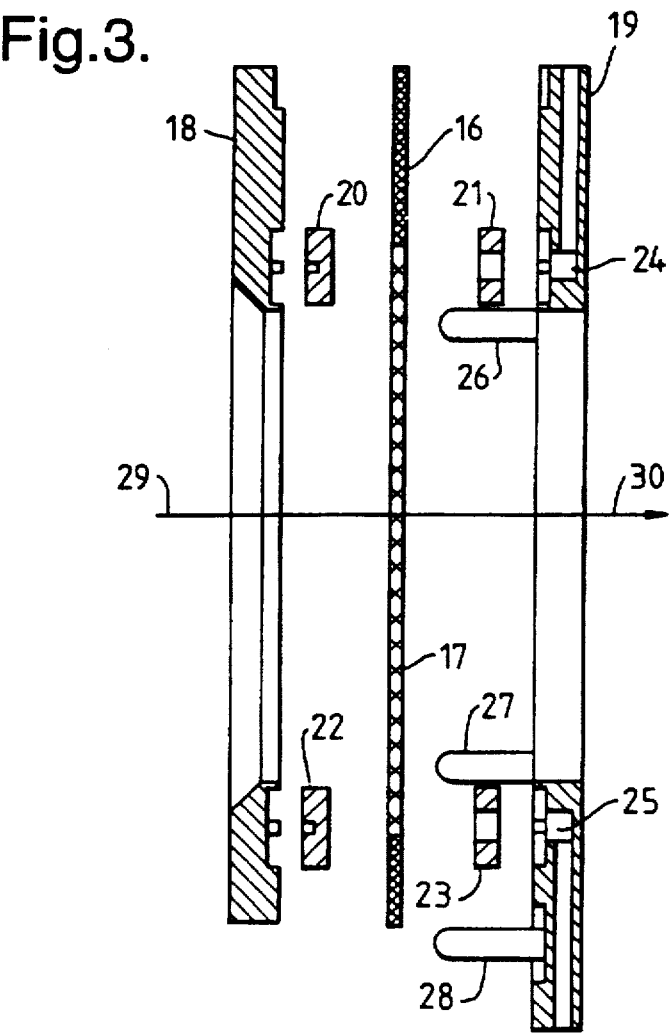
FIG. 3: shows a cross section of a cassette of the invention in a maintained gradient format.

In FIG. 3 there is shown a cross section through the arrangement of front and back plates of the gradient former prior to their association with a gel cassette of the invention and appropriate gaskets. The gel cassette frame (16) and gel body therein (17) are held between the front (18) and back (19) plates of the former such that elongate gaskets (20, 21, 22, 23) are provided to engage the PVC around slits made in the PVC film, within the cassette windows adjacent their top and bottom, and the former plates. The gaskets (21, 23) between the cassette and the back plate are such that they are aligned with inlets (24, 25) from small reservoirs therein which are in turn connected to larger reservoirs of medium of desired chemical or physical property. Plate guides (26, 27, 28) are provided on the back plate for engaging holes in the front plate such that windows in each plate which correspond in size approximately to the window in the cassette are aligned with each other such as to allow laser light to pass generally in the direction from the laser source side (29) to the detector side (30). It will be realised that in use the cassette and the plates will be at about 45° and thus the line (29) (30) passes at an angle through the combination. One of the plates has mounting holes for attaching the complete assembly to the X/Y stage.

Figure 4:
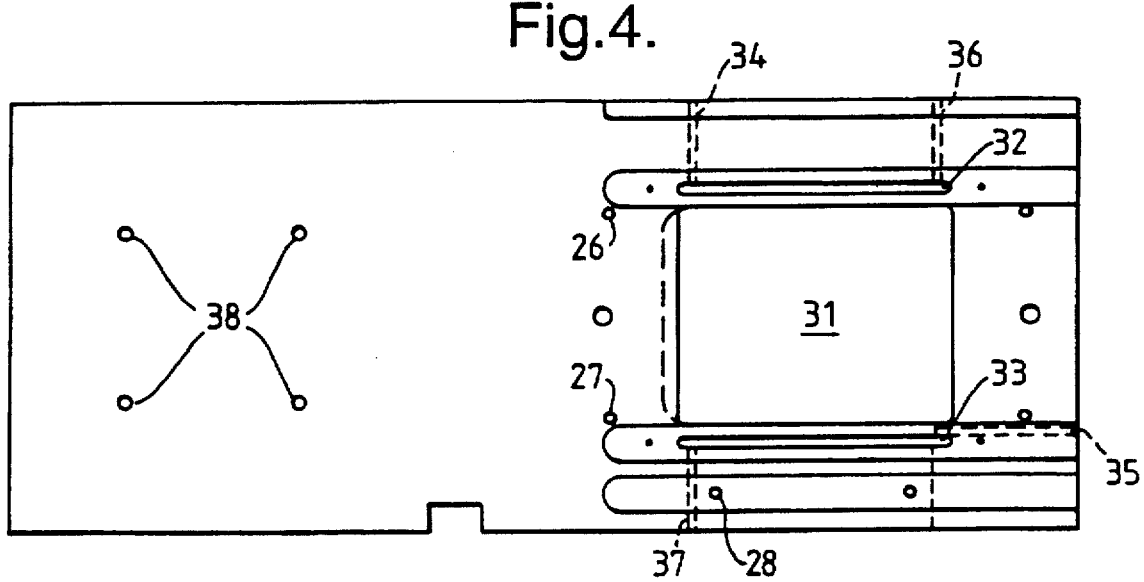
FIG. 4: shows a front elevation of the back plate of the gradient former of the invention with inlet, outlet and reservoir positions shown.

FIG. 4 shows a front elevation of the back plate wherein window (31) is provided between inlets (32, 33) from reservoirs which are in turn connected by inlets from larger reservoirs (34, 35) and flush outlets (36, 37). Holes (38) for mounting the plate onto the X-Y stage are provided on an extension on one side of the reservoir/window area, while the guides (26, 27, 28) are provided about the window and bottom reservoir.

EXAMPLE 5

The laser gel scanner (LGS) system.

Figure 2:
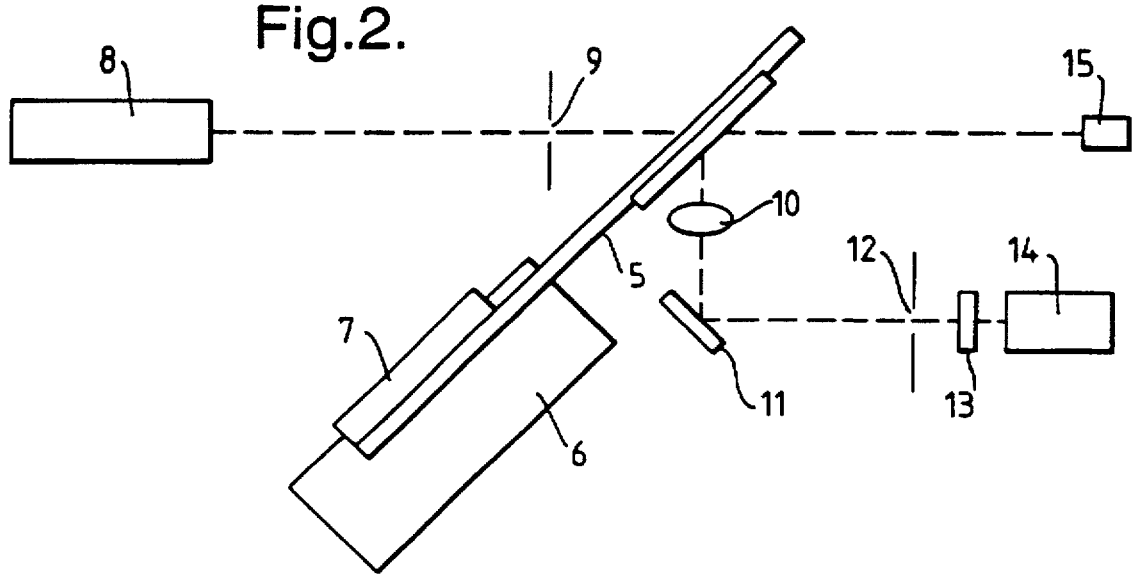
FIG. 2: is a diagrammatic representation of the light scattering and processing apparatus of the invention, as described further in Example 5

The light processing apparatus (see FIG. 2) consisted of a vertical mount plate (5) in which the cassette was held vertically on a motorised X-Y stage (Micro-Control): X-stage (6) and Y-stage (7). The cassette was illuminated by a 30 mW He-Ne laser (8) (Spectra Physics) at a wavelength of 632.8 nm. The laser beam was collimated by a 200 μm pinhole (9) mounted as close to the cassette (2 cm) as possible. This provided a well defined diameter and a sharp beam profile, and illuminated each pixel as evenly as possible. Measuring total light scattered through 90° from each pixel did not maximise sensitivity. Contributions to the total scattered light intensity from any point on the cassette when illuminated by a 0.2 mm laser beam were from many sources, including the 2 cassette windows and the gel itself.

Light scattering contribution made by a few bacteria of combined diameter of approximately 10 μm is very small but if the path of the laser through the cassette is interrogated a small section at a time. for example 200 μm, then the contribution from the bacteria is much greater. In the order to facilitate this the laser beam was passed through the cassette at an angle of 45° giving a path length in the gel of 2.8 mm. Light scattered through 90° from the laser beam was collected and focused by a ×10 microscope objective (10) placed 2 cm from the cassette. The scattering angle was set at 90° because this was the only way of maintaining a focused image of the laser beam throughout the thickness of the cassette and to keep the distance between the scattering centre and detector as similar as possible along the length of the beam in the gel, thus providing a similar solid angle for light collection at all points along the beam. The cassette was mounted such that light was reflected away from the detection system so that only scattered light was detected. The lens focused the image of the laser beam going through the cassette onto a 400 μm pinhole (12). Between the lens and the pinhole was a scanning mirror (11) which could move the focused image of the laser beam across the pinhole. Directly behind the pinhole was a narrow band pass filter (13) to remove any stray background light.

Light passing through the filter was detected by a photomultiplier tube (14) (Hamamatsu) (PMT). The signal from the PMT was fed to a fixed gain preamplifier and thence to a variable filter (KEMO Ltd.) and 12 bit analogue to digital converter (ADC). The filter was a variable 24 dB Butterworth type set to low pass with a cutoff at 2 kHz. The filter had a variable gain amplifier which could be set to 1, 3 or 10 times gain, allowing an effective increase in the dynamic range available through the ADC by a factor of 10. The dynamic range in intensity available to the controlling computer was 4095, in any given run. However, over a series of runs such as would be made when following colony size as a function of time this could be improved upon. In the early stages of growth the scattered intensity was low and high gain was required and the filter gain was set to 10. In the later stages of growth the scattered intensity was high and low gain was needed so the filter gain was set to 1. This approach gave an effective dynamic range of 40950. The X-Y stage was driven by a CC1.2 2-axis stepper motor controller (Micro-Control) and the scanning mirror controlled through a 12 bit digital to analogue converter (DAC). The three peripheral devices, the ADC, DAC and the CC1.2 were driven from a VME based microcomputer (Microsys). Control software was written in both Fortran and 68000 assembler code. The computer accessed the peripherals via an on board 68230 parallel interface. A beamstop (15) was provided for capturing unscattered light.

For the purposes of measurement the scan window (area of the cassette to be interrogated) was broken into pixels the size of which were set by the laser beam diameter passing through the cassette (i.e. 200 μm). The cassette was scanned in horizontal raster fashion by driving the X-Y stage 0.28 mm in the X direction or 0.2 mm in the Y direction from one pixel to the next. At each pixel position the scanning mirror moved the laser beam image across the detector pinhole and back again. This scan was broken down into 100 separate readings but for reasons of phase lag only 60 were used. Each reading took approximately 100 μs so the effective mirror drive frequency was 100 Hz which gave a phase lag between the mirror drive signal and the mirror position of about 1 mS or 10 readings.

The stages have a resolution of 10 μm per step and a maximum start frequency of 400 Hz. Because the mirror scan was slower than one half step the stage could only be run at the maximum start speed. Moving the 28 steps from one pixel to the next thus took 70 ms plus the mirror scan of 10 ms giving a pixel scan frequency of about 12 Hz or 2 μl/S in a 2 mm thick cassette. At each pixel position the minimum intensity value plus the threshold value were subtracted from all 60 data values and resultant negative values were set to zero. Any peaks in the remaining data were then stored so that the final data was in the form of an X-position, a Y-position and an intensity value. The upper limit on the number of peaks detected is 25000 due to memory limitations. The growth of bacterial colonies was monitored by regular measurement of the light scattered through 90° from the colonies. The scattered intensity was then related to colony radius and colony viable count from previous calibration measurements. Measurements of scattered intensity were also made as a function of position within the cassette.

EXAMPLE 6

Analysis of data.

It was assumed that the scattered intensity was proportional to the square of the colony radius and that the number of viable bacteria in a colony was proportional to the cube of the radius. Thus in theory we have a dynamic range of about 200 for radius and about 8×10$^6$ for numbers of viable bacteria. Intensity data was treated simplisticly by integration over all pixels in the area of the cassette window that was scanned and conversion to intensity per unit volume (ml) as in Equation 1. Equations 2 and 3 were then applied to give colony radius and numbers of viable bacteria at the time of each measurement.

EQUATIONS $$I = \Sigma_i \tag{1}$$

$$R = K_r / N(I-I_o)^{0.5} \tag{2}$$

$$V = K_n(I-I_o)^{1.5} \tag{3}$$

where R is the colony radius and Vc is the number of viable bacteria per ml. I is the measured intensity per ml. $K_n$ and $K_r$, are proportionality constants. $N_{col}$ is the number of colonies per ml, $I_o$ is the integrated background scattering from everything except the bacteria.

The exempliifed LGS was not designed to detect single bacteria and hence provided no useful data in the lag phase. The latter part of the exponential and the stationary phases could be monitored, and if the initial inoculation concentration in the cassette was known then the lag phase could be deduce. In order to provide any of these parameters the LGS intensity data must be converted into growth curves by the application of Equation 3. The value of $K_n$ from this equation must be deduced empirically as must the value of $K_r$ in equation 2.

EXAMPLE 7

Growth of *Salmonella typhimurium* Strain LT2 in cassettes:

Cassettes were constructed that contained culture medium adjusted to pH 7.0, and with either 0.5 or 3.5% (w/v) NaCl and inoculated with *S. typhimurium* at a concentration of approximately $10^3$ ml$^{-1}$. One cassette was scanned in the LGS constantly throughout incubation. Other cassettes, prepared and incubated in parallel, were used for the determination of the numbers of viable bacteria, using conventional plating techniques, or for the measurement of colony diameter using a light microscope fitted with Normarski optics.

LGS data from cassettes that contained 0.5 or 3.5% (w/v) NaCl show the typical form for a bacterial growth curve with an initial lag phase followed by an exponential growth phase and finally a stationary phase. In order to extract the values for $K_n$ at the two different NaCl concentrations these curves were fitted to the corresponding plate count data using standard nonlinear least squares techniques. The following conditions were applied when fitting for $K_n$: firstly $I_o$ the background had to be included as a fit parameter, and secondly as the times for the LGS and the viable count data did not coincide the LGS results had to be interpolated to the times for the viable counts. The interpolated LGS data were then fitted to the data via Equation 3.

The result of Equation 3 at the original LGS times were calculated using the values of $K_n$ and $I_o$ obtained from the fit. The only variable parameters in the fit were $K_n$ and $I_o$, the values for which were $4.9 \times 10^{-3}$ and $1.41 \times 10^5$ respectively for the 0.5% NaCl and $4.94 \times 10^{-3}$ and $1.0 \times 10^5$ for the 3.5% NaCl; both curves being in agreement. A similar approach was taken to the radius data, and the interpolated LGS data was fitted using Equation 2 to the measured colony radii. In the fits of Equation 2 the values of $I_o$ used were those obtained from the fits of the viable count data and $K_r$ was the only floating parameter. $N_{col}$ was obtained from a viable count of a cassette at the time of inoculation. For the 0.5% NaCl LGS cassette the initial inoculum was 800 ml$^{-1}$ and the value obtained for $K_r$ was 13.0. The initial inoculum for the 3.5% NaCl cassette was a little lower at 300 ml$^{-1}$ and the fitted $K_r$ was 5.8. The growth parameters obtained from all four curves show good agreement between the measured size and that calculated from the LGS data.

The data obtained demonstrated the usefulness of the LGS system for the continuous automated determination of the rate of growth of bacteria within a colony. The mean size of stationary phase colonies in medium containing 3.5% NaCl was larger than in medium containing 0.5% NaCl. The numbers of viable bacteria in colonies growing in the higher salt concentration was lower, however, than in the low salt. This may have been due to death of cells within the colony, or differences in the size or packing of cells, but demonstrated the necessity of assigning different values to the proportionality constants in equations 2 and 3.

We claim:

1. A method for determining the characteristics of a material with respect to its ability to kill, inhibit growth or support growth of microorganisms, comprising determining the presence and/or amount of microorganisms in a body of the material or a material having one or more analogous properties as a growth media thereto by passing a beam of laser light through it, processing laser light scattered by the material at a set angle or angles to provide a signal indicative of the amount and/or type of scattering, and relating this to the presence and/or amount of microorganisms, wherein the body comprises a solid or semi-solid medium of predetermined composition and dimension and the change in the presence and/or amount of microorganism at a given locus of the body between two or more temporally spaced determinations is related to said characteristics of the material.

2. The method as claimed in claim 1 wherein the content of the body of material comprises a gradient with respect to the amount of one or more agents.

3. The method as claimed in claim 1 wherein the body of material is communicated with one or more sources of agents, the effect of which on microorganism viabilty or growth is to be studied.

4. The method as claimed in claim 3 wherein the agents are passed from two or more sources at opposite ends and/or sides of the body such as to set up a gradient across the body varying in agent content.

5. The method as claimed in claim 1 wherein the body is communicated with a gas or a predetermined humidity through its sides.

6. The method as claimed in claim 2 wherein the gradient is one of a drug, pH, salt or nutrient.

7. The method as claimed in claim 1 wherein the body of the material is provided with at least two substantially parallel opposed external surfaces through which the beam is passed.

8. The method as claimed in claim 7 wherein two of the parallel opposed external surfaces are oriented at about 45° to the incident laser beam and the light scattered through about 90° is collected for processing purposes.

9. The method as claimed in claim 1 claims wherein the body is mounted such that light is reflected away from the processing means so that only scattered light is processed.

10. The method as claimed in claim 1 wherein the light is collected using a magnifying lens and then focused onto a photomultiplier or CCD device.

11. The method as claimed in claim 10 wherein the light is focused onto a pinhole for collimation into a photomultiplier.

12. The method as claimed in claim 10 wherein the light is focused onto a scanning device which directs it toward a photomultiplier.

13. The method as claimed in claim 10, wherein a light filtering means is placed between the lens and photomultiplier for removing stray background light.

14. The method as claimed in claim 10 wherein the photomultiplier or CCD produces a signal proportional to the collected scattered light and passes this to a processor unit whereby it can be stored and/or manipulated for deriving information relative to other measurements from the body, other bodies or later derived signals from either.

15. The method as claimed in claim 1 wherein the laser light is collimated and scanned across the body stepwise such that the body is studied in the form of a number of pixels.

16. A method as claimed in claim 15 wherein the scanning is achieved by mechanically moving the body of material relative to the beam and light processor.

17. A method for determining the presence and/or amount and/or characteristics of a microorganism in a material, said method comprising the steps of inoculating a solid or semi-solid medium with a sample of the material, forming the inoculated medium into a body of predetermined dimension, passing a beam of laser light through the body, processing laser light scattered by a given locus of the body at a set angle or angles to provide a signal indicative of the amount and/or type of scattering and relating this to the presence and/or amount of microorganism and relating the change in presence and/or amount of the microorganism at that locus between two or more temporally spaced signals to said characteristics of the microorganism.

18. The method as claimed in claim 17 wherein the characteristics of the microorganism are determined and compared with those obtained for known microorganism using a method as claimed in any one of claims 1 to 17.

19. The method as claimed in claim 17 wherein the body of material varies in its composition and thus ability to support or inhibit microorganism growth.

20. The method as claimed in claim 17, wherein there is provided a gradient of one or more agents across the body, or the body is exposed such agents in the form of a particular atmosphere contacting its outer surface.

21. A cassette for use in a method for determining the characteristics of a material with respect to its ability to kill, inhibit growth or support growth of microorganisms, comprising determining the presence and/or amount of microorganisms in a body of the material or a material having one or more analogous properties as a growth media thereto by passing a beam of laser light through it, processing laser light scattered by the material at a set angle or angles to provide a signal indicative of the amount and/or type of scattering, and relating this to the presence and/or amount of microorganisms, wherein the body comprises a solid or semi-solid medium of predetermined composition and dimension and the change in the presence and/or amount of microorganism at a given locus of the body between two or more temporally spaced determinations is related to said characteristics of the material, in which said cassette comprises a container including two opposed substantially parallel retaining surfaces of laser transmitting material situated on either side of an interior volume, the cassette being provided with a sealable means for filling that volume with a solid or semi-solid material without damaging the retaining surfaces over at least a substantial area thereof.

22. The cassette as claimed in claim 21 comprising a rigid frame with window apertures coinciding with the retaining surfaces over at least part of their area such that a laser beam can traverse the material inside the cassette in use.

23. The cassette as claimed in claim 21 wherein the two opposed retaining surfaces are separated about 1 to 5 mm.

24. The cassette as claimed in claim 21 wherein the retaining surfaces are provided by thin plastics films.

25. The cassette as claimed in claim 24 wherein the frame is enveloped with a sleeve of heat shrinkable plastics film that has been heat sealed at its ends and heat shrunk into engagement with the frame.

26. The cassette as claimed in claim 21 characterised in that it is filled with a microbial growth support medium.

27. The cassette as claimed in claim 26 wherein the medium has been sterilized and then inoculated with microorganism to be studied.

28. The cassette as claimed in claim 26 wherein the microbial growth support medium is provided in the form of a series of different zones is created across the area of the cassette window; the zones having distinct physical and/or chemical characteristics.

29. The cassette as claimed in claim 28 wherein at least one end of the medium filled cassette is communicated with a reservoir of material having desired chemical composition.

30. The cassette as claimed in claim 29 wherein the other end of the cassette is also communicated with a reservoir of material of desired chemical composition, of varying parameter to the first, such that a gradient of constant slope with respect to a given chemical or physical state is created and/or maintained.

31. The cassette as claimed in claim 21 wherein the sealable means for filling the volume comprises an aperture in the frame that is an extension of the volume such that making an incision in the film by the aperture allows access to the volume without damaging the film forming the retaining surfaces.

32. The cassette as claimed in claim 21 wherein the cassette is permeable to gases such that exterior gases can access its interior volume.

33. An apparatus for use in a method for determining the characteristics of a material with respect to its ability to kill, inhibit growth or support growth of microorganisms, comprising determining the presence and/or amount of microorganisms in a body of the material or a material having one or more analogous properties as a growth media thereto by passing a beam of laser light through it, processing laser light scattered by the material at a set angle or angles to provide a signal indicative of the amount and/or type of scattering, and relating this to the presence and/or amount of microorganisms, wherein the body comprises a solid or semi-solid medium of predetermined composition and dimension and the change in the presence and/or amount of microorganism at a given locus of the body between two or more temporally spaced determinations is related to said characteristics of the material, said apparatus comprising a source of laser light, a mounting for supporting a body comprising solid or semi-solid material at a desired angle such that it can be addressed by the laser light emitted by the source, and a means for processing light scattered by the material over a predetermined angle and producing a signal therefrom; wherein the apparatus is adapted to scan the laser light through all or part of the material.

34. An apparatus as claimed in claim 30 wherein the mounting is adapted to support a cassette as claimed in any one of claims 17 to 27.

35. The apparatus as claimed in claim 33 wherein the mounting supports the material in a chamber capable of maintaining it in desired environmental conditions.

36. The apparatus as claimed in claim 35 wherein the desired environmental conditions may be varied with regard to temperature, humidity and/or gaseous content.

* * * * *